United States Patent
Kelso et al.

(10) Patent No.: US 10,501,735 B2
(45) Date of Patent: Dec. 10, 2019

(54) DEVICE WITH CONTROLLED FLUID DYNAMICS, FOR ISOLATION OF AN ANALYTE FROM A SAMPLE

(71) Applicants: Northwestern University, Evanston, IL (US); Quidel Corporation, San Diego, CA (US)

(72) Inventors: David M. Kelso, Wilmette, IL (US); Kunal Sur, Evanston, IL (US); Tom Westberg, Gurnee, IL (US); Zaheer Parpia, Evanston, IL (US); Mark J. Fisher, Highland Park, IL (US)

(73) Assignees: Quidel Corporation, San Diego, CA (US); Northwestern University, Evanston, IL (US)

( * ) Notice: Subject to any disclaimer, the term of this patent is extended or adjusted under 35 U.S.C. 154(b) by 0 days.

(21) Appl. No.: 13/972,788

(22) Filed: Aug. 21, 2013

(65) Prior Publication Data

US 2014/0057271 A1    Feb. 27, 2014

Related U.S. Application Data

(60) Provisional application No. 61/692,657, filed on Aug. 23, 2012.

(51) Int. Cl.
*C12N 15/10* (2006.01)
*B01L 3/00* (2006.01)

(52) U.S. Cl.
CPC .... *C12N 15/1006* (2013.01); *B01L 3/502753* (2013.01); *B01L 3/502761* (2013.01);
(Continued)

(58) Field of Classification Search
CPC ........... C12N 15/1006; B01L 3/502753; B01L 3/502761; B01L 2300/087; B01L 2300/0851; Y10T 436/25375
See application file for complete search history.

(56) References Cited

U.S. PATENT DOCUMENTS

| 4,921,612 A | 5/1990 | Sirkar |
| 5,230,866 A | 7/1993 | Shartle et al. |

(Continued)

FOREIGN PATENT DOCUMENTS

| DE | 102009035941 A1 | 2/2011 |
| EP | 1707965 A1 | 4/2006 |

(Continued)

OTHER PUBLICATIONS

Chin et al., "Communication to the editor on protein solubility in organic solvents", Biotechnology and Bioengineering vol. 44, pp. 140-145 (1994).

(Continued)

*Primary Examiner* — Samuel P Siefke
(74) *Attorney, Agent, or Firm* — Casimir Jones SC; David W. Staple

(57) ABSTRACT

Devices for use in extracting an analyte of interest from a sample are described. In one embodiment, a device is comprised of a first plurality of chambers, where one or more chambers in the plurality of chambers has a deep end and a shallow end with a depth $d_1$. A channel disposed between at least two adjacent chambers in the plurality of chambers has a depth greater than $d_1$. The dimensions of the chamber and channel provide control of fluid movement in the device, particularly when introducing fluid into the device for its use and during use of the device.

11 Claims, 10 Drawing Sheets

(52) U.S. Cl.
CPC . *B01L 2300/087* (2013.01); *B01L 2300/0851* (2013.01); *Y10T 436/25375* (2015.01)

(56) References Cited

U.S. PATENT DOCUMENTS

| | | | |
|---|---|---|---|
| 5,238,810 | A | 8/1993 | Fujiwara et al. |
| 5,279,936 | A | 1/1994 | Vorpahl |
| 5,466,575 | A | 11/1995 | Cozzette et al. |
| 6,040,193 | A | 3/2000 | Winkler et al. |
| 6,989,237 | B2 | 1/2006 | Fulwyler et al. |
| 7,354,750 | B2 | 4/2008 | Simpson et al. |
| 7,745,129 | B1 | 6/2010 | Schatz |
| 7,820,454 | B2 | 10/2010 | Su et al. |
| 8,187,808 | B2 | 5/2012 | Kelso et al. |
| 8,206,918 | B2 | 6/2012 | Kelso et al. |
| 2001/0029810 | A1 | 10/2001 | Ho |
| 2002/0151040 | A1 | 10/2002 | O'Keefe et al. |
| 2004/0011650 | A1 | 1/2004 | Zenhaursern et al. |
| 2005/0191759 | A1 | 9/2005 | Pedersen-Bjergaard et al. |
| 2005/0202504 | A1 | 9/2005 | Anderson et al. |
| 2005/0266429 | A1 | 12/2005 | Kleiber et al. |
| 2006/0134793 | A1 | 6/2006 | Key |
| 2007/0036679 | A1 | 2/2007 | Munenaka |
| 2007/0184463 | A1 | 8/2007 | Molho et al. |
| 2008/0160639 | A1 | 7/2008 | Su et al. |
| 2008/0217246 | A1 | 9/2008 | Benn et al. |
| 2008/0226500 | A1 | 9/2008 | Shikida et al. |
| 2008/0254467 | A1 | 10/2008 | Regan |
| 2008/0277348 | A1 | 11/2008 | Izumizawa |
| 2009/0023201 | A1 | 1/2009 | Hongo et al. |
| 2009/0148933 | A1 | 6/2009 | Battrell et al. |
| 2009/0220948 | A1 | 9/2009 | Oviso et al. |
| 2009/0246782 | A1 | 10/2009 | Kelso et al. |
| 2009/0289213 | A1 | 11/2009 | Pipper et al. |
| 2009/0323069 | A1 | 12/2009 | Naessens et al. |
| 2010/0120083 | A1 | 5/2010 | Ritzen et al. |
| 2010/0273142 | A1 | 10/2010 | Prins et al. |
| 2010/0291666 | A1 | 11/2010 | Collier et al. |
| 2011/0053202 | A1* | 3/2011 | Parng ............ B01L 3/502746 435/29 |
| 2011/0212509 | A1 | 9/2011 | Beebe et al. |
| 2011/0213133 | A1 | 9/2011 | Beebe et al. |
| 2011/0306109 | A1* | 12/2011 | Kelso ............ B01L 3/502761 435/173.7 |
| 2012/0107811 | A1 | 5/2012 | Kelso et al. |
| 2013/0158240 | A1 | 6/2013 | Beebe et al. |

FOREIGN PATENT DOCUMENTS

| | | | |
|---|---|---|---|
| EP | 2353721 | A2 | 8/2011 |
| FR | 2858688 | A1 | 2/2005 |
| JP | 2003-290682 | A | 10/2003 |
| KR | 1020020021810 | A | 3/2002 |
| WO | WO 2005/069015 | A1 | 7/2005 |
| WO | WO 2005/108620 | A2 | 11/2005 |
| WO | WO 2006/071770 | A2 | 7/2006 |
| WO | WO 2007/102785 | A1 | 9/2007 |
| WO | WO 2008/123112 | A1 | 10/2008 |
| WO | WO 2009/105711 | A1 | 8/2009 |
| WO | WO 2009/111316 | A2 | 9/2009 |
| WO | WO 2010/091246 | A2 | 8/2010 |
| WO | WO 2011/015454 | A1 | 2/2011 |
| WO | WO 2011/123064 | A1 | 10/2011 |
| WO | WO 2013/169730 | A1 | 11/2013 |

OTHER PUBLICATIONS

Dineva et al., "Sample preparation: a challenge in the development of point-of-care nucleic acid based assays for resource-limited settings", Analyst, vol. 132, pp. 1193-1199 (2007).

Furlani and Ng, "Analytical model of magnetic nanoparticle transport and capture in the microvasculature", Physical Review E73, 061919-1-061919-10, 12 pgs. (2006).

International Search Report from PCT Patent Application No. PCT/US2013/039846 dated Aug. 20, 2013.

Liu et al., "Self-contained, fully integrated biochip for sample preparation, polymerase chain reaction amplification and DNA microarray detection", Analytical Chemistry, vol. 76, pp. 1824-1831 (2004).

Mylonakis et al., "Plasma viral load testing in the management of HIV infection", Am. Fam. Physician vol. 63, No. 3, pp. 483-490 (2001).

Pipper et al., "Catching bird flu in a droplet", Nature Medicine, vol. 13, No. 10, pp. 1259-1263 and supplementary information, Fig. 1-5, pp. 1-5 (2007).

Shikida et al., "Development of an enzymatic reaction device using magnetic bead-cluster handling", J. Micromech. Microeng., vol. 16, pp. 1875-1883 (2006).

International Search Report from related PCT Patent Application No. PCT/US2013/056055 dated Nov. 29, 2013.

International Search Report from related PCT Patent Application No. PCT/US2013/039880 dated Oct. 25, 2013, application now published as WO2013/169730 on Nov. 14, 2013.

* cited by examiner

DEVICE WITH CONTROLLED FLUID DYNAMICS, FOR ISOLATION OF AN ANALYTE FROM A SAMPLE

CROSS-REFERENCE TO RELATED APPLICATIONS

This application claims the benefit of U.S. Provisional Application No. 61/692,657, filed Aug. 23, 2012, incorporated herein by reference in its entirety.

TECHNICAL FIELD

The subject matter described herein relates to a device for use in sample treatment and analysis applications, where the device is designed for control of fluid dynamics within the chambers and channels of the device.

BACKGROUND

Analysis of biological entities, such as proteins and nucleic acids, in biological samples generally requires that the target entity in question first be isolated from the biological matrix, which frequently includes a complex mixture of non-target substances. The effective isolation of analytes is a prerequisite for efficient downstream analysis of the analyte, including, for example, amplification of a nucleic acid for detection and quantification or identification of a protein or enzyme. It is also important, in many cases, such as in nucleic acid amplification, that the isolated species not contain residues of certain reagents and/or solvents used during isolation.

Existing methods of isolation frequently involve multi-step processes, often requiring multiple extraction and/or centrifugation steps, which require trained personnel and can introduce risks of contamination and/or loss of sample. A need exists for a self-contained device that is effective to isolate an analyte from a biological sample, such as obtained from a patient, with minimal operator manipulation of sample and reagents.

BRIEF SUMMARY

The following aspects and embodiments thereof described and illustrated below are meant to be exemplary and illustrative, not limiting in scope.

In one aspect, a device as described herein is provided. In another aspect, methods of using a device as described herein for isolation or extraction of a target analyte from a sample is provided.

In another aspect, a device comprising a first plurality of chambers is provided, where one or more chambers in the plurality of chambers has a deep end and a shallow end with a depth $d_1$. A channel is disposed between at least two adjacent chambers in the plurality of chambers, the channel having a depth greater than $d_1$.

In one embodiment, the chambers in the plurality of chambers are serially positioned and each chamber is the plurality is separated by a channel.

In another embodiment, the first plurality of chambers is comprised of at least three chambers, wherein two chambers in the plurality have a deep end and a shallow end with a depth $d_1$, and wherein the channel is disposed between the two chambers having the shallow end with a depth $d_1$.

In yet another embodiment, the first plurality of chambers is comprised of at least five chambers, wherein three chambers in the plurality have a deep end and a shallow end with a depth $d_1$, and wherein the channel is disposed between two chambers having the shallow end with a depth $d_1$.

In still another embodiment, each chamber in the plurality of chambers has a volume, wherein the volume of one chamber in the plurality of chambers differs from the volume of another chamber in the plurality.

In another embodiment, the one or more chambers in the plurality of chambers with a deep end and a shallow end with a depth $d_1$ has a floor and a side wall that meet to define four corners, and wherein at least the corners in the deep end of the chamber are rounded.

In another embodiment, the one or more chambers in the plurality of chambers with a deep end and a shallow end with a depth $d_1$ has a floor and a side wall that meet to define four corners, and wherein at least the corners in the shallow end of the chamber are angled.

In yet another embodiment, the device further comprises a cover having an access port in fluid communication with a chamber in the plurality of chambers. In one embodiment, the access port is in fluid communication with the one or more chambers in the plurality of chambers having a deep end and a shallow end with a depth $d_1$, and wherein the access port is positioned for introduction of fluid directly into the deep end of the chamber.

In another embodiment, the device comprises a second plurality of chambers. One or more chambers in the second plurality of chambers has a deep end and a shallow end with a depth $d_1$, and a channel disposed between at least two adjacent chambers in the second plurality of chambers, the channel having a depth greater than $d_1$.

In one embodiment, the first and second plurality of chambers are linearly parallel.

In another aspect, a method for extracting an analyte of interest from a sample is provided. The method comprises providing a device as described herein, introducing a sample into a first chamber of the device, the first chamber or the sample upon its introduction comprising a solid carrier member capable interacting with an analyte of interest in the sample, thus forming a carrier-analyte complex; and moving the carrier-analyte complex from the first chamber into a second chamber, wherein said moving transverses the channel filled with a fluid.

In one embodiment, the channel is filled with a gas or a liquid.

In another embodiment, the channel is filled with air or with a water-immiscible liquid.

In still another embodiment, the method further comprises dispensing a liquid into one or more chambers in the plurality of chambers.

In yet another embodiment, dispensing a liquid comprises dispensing a lysis solution, a wash solution, or an elution solution.

In one embodiment, the method comprises dispensing a liquid into the first chamber of the device prior to introducing a sample.

In another embodiment, the method comprises dispensing a water-immiscible substance into the channel.

In still another embodiment, during moving of the carrier-analyte complex from a first chamber to a second chamber, the water immiscible liquid in the channel remains stationary.

In addition to the exemplary aspects and embodiments described above, further aspects and embodiments will become apparent by reference to the drawings and by study of the following descriptions.

Additional embodiments of the present devices and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1:
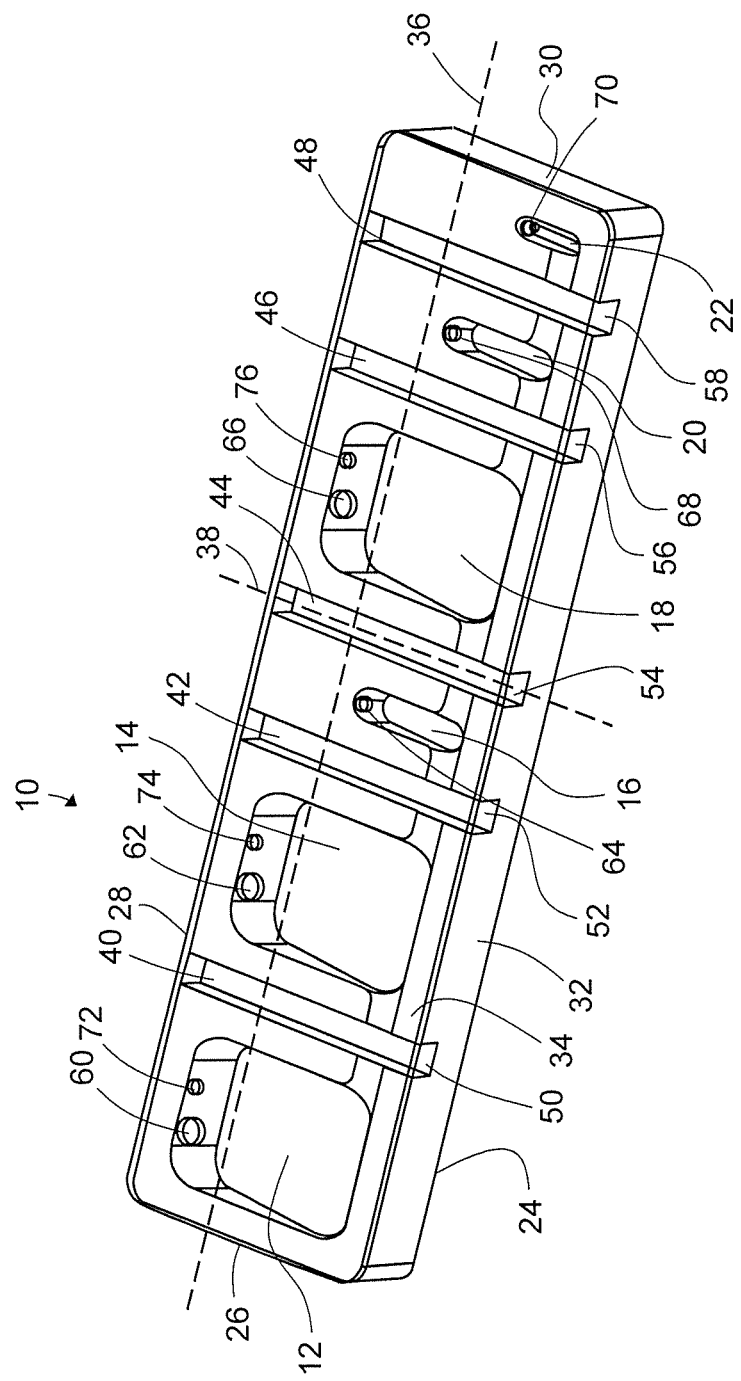
FIG. 1 is a device or cartridge in accord with one embodiment.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to an "excipient" includes a single excipient as well as two or more of the same or different excipients, and the like.

As pertains to the present disclosure, a "biological sample" can include a tissue sample or a body fluid sample, which includes liquid, solid, and semisolid samples, e.g. blood, blood components such as plasma or serum, urine, saliva, sputum, mucous, amniotic fluid, semen, vaginal secretions, tears, spinal fluid, washings, feces, biopsy specimens, skin, nails, and hair.

An "isolated" analyte is one that has been separated from other constituents with which it is associated in a sample, such that it can be detected with a desired degree of accuracy and precision. The isolated analyte is typically dissolved in a solvent medium that may also contain non-interfering substances. In the case of a biological sample, the analyte is isolated from cellular constituents with which it is normally associated, and from other types of cells which may be present in the sample.

A "liquid reagent", as the term is used herein, refers to any liquid contained within any of the chambers of the device as described herein, including aqueous, nonaqueous, and water-immiscible liquids.

A "reagent solution" typically refers to an aqueous solution. The "reagent" may be a chemical or biological substance that causes a chemical change to a sample component, or it may be simply a buffering agent, a salt, or a solvent.

II. Device

Disclosed herein, in one aspect, is a device for extraction of an analyte of interest from a sample or matrix suspected of containing the analyte. In one embodiment, the sample is a biological sample. In other embodiments, the sample can be an environmental sample. The analyte can be for example, as described further below, a protein, a nucleic acid, a cell or cell component, or a toxin.

Isolation of an analyte using the device described herein can be done manually or in an automated or semi-automated manner. For automated or semi-automated use, the device can be used in conjunction with an instrument such as described further below.

One embodiment of the device, also sometimes referred to as a cartridge, is shown in FIG. 1. A planar device 10 is comprised of at least one chamber, and preferably at least two chambers, and preferably a plurality of chambers, such as chambers 12, 14, 16, 18, 20 and 22 in device 10. In one embodiment, the term "plurality" intends three or more. Planar device 10 also includes a bottom wall or floor 24, side walls 26, 28, 30, and 32 and a cover 34. Device 10 has a certain length, l, width, w, and thickness, t, giving it a three-dimensional functionality. The device length defines a longitudinal axis, denoted in FIG. 1 by a dashed line 36. The device width defines a horizontal axis, denoted in FIG. 1 by a dashed line 38.

Device 10 also comprises one or more channels positioned between adjacent chambers, preferably positioned between a pair of adjacent chambers. In the embodiment shown in FIG. 1, channels 40, 42, 44, 46 and 48 are exemplary of an embodiment where a channel is disposed between each chamber in the device. That is, channel 40 is positioned between chamber 12 and chamber 14; channel 42 is positioned between chamber 14 and chamber 16; channel 44 is positioned between chamber 16 and chamber 18; channel 46 is positioned between chamber 18 and chamber 20; and channel 48 is positioned between chamber 20 and chamber 24. It will be appreciated that the embodiment of FIG. 1 is merely exemplary, as there need not be a channel positioned between each pair of adjacent chambers. It will also be appreciated that the terminology "channel" is not intended to be limiting to the dimensions or shape of the structure, as the structure can be of nearly any shape or dimension.

The one or more channels in the device may have an opening or vent to the surrounding atmosphere, and during preparation of the device for use in an extraction procedure and during the extraction procedure, the channels are filled with a gas, preferably air. In this respect, the channel serves during use of the device, which encompasses preparation of the device for use to isolate an analyte and the actual isolation of the analyte (which may encompass detection), as an air gap between fluid filled chambers, as will be further described below. In the embodiment shown in FIG. 1, device 10 comprises openings access ports 50, 52, 54, 56 and 58, associated with each of the respective channels.

In one embodiment, one or more of the channels may have an input region and an output region, the input region receiving fluid from a first, adjacent chamber, and the output region communicating with a second chamber downstream of the first chamber, for conveying the fluid thereto. The input region of the channel may be larger than the output region. That is, the channel as it extends from its input region to its output region is tapered, with the input region having a larger width than the output region.

The cover 34 in device 10 can be fixed onto the device or can be removable from the device. In a preferred embodiment, the cover is transparent, to permit a user to view the contents in the chambers and channels of the device. The cover also includes one or more openings positioned for access to at least one chamber in the device, and preferably positioned for access to each chamber individually. In the embodiment shown in FIG. 1, device 10 comprises access ports 60, 62, 64, 66, 68 and 70, associated with chambers 12, 14, 16, 18, 20 and 22, respectively. The access ports are dimensioned to permit insertion of, for example, a pipette, syringe, tube, swab, or other instrument through the cover to introduce or remove fluid from a chamber. The top cover additionally and optionally comprises a vent associated with chambers wherein a fluid is intended to be introduced, replaced, replenished or manipulated prior to or during use of the device, as will be further described. In the embodiment shown in FIG. 1, device 10 comprises vents 72, 74, and 76, associated with chambers 12, 14, and 18, respectively.

It will be appreciated that provision of access ports in the 'top' of the device permits the device to be used in conjunction with a robotic fluid handling system, where a robotic arm(s) with one or more pipettes interacts with the access ports to dispense liquid into or out of a chamber.

Figure 2:
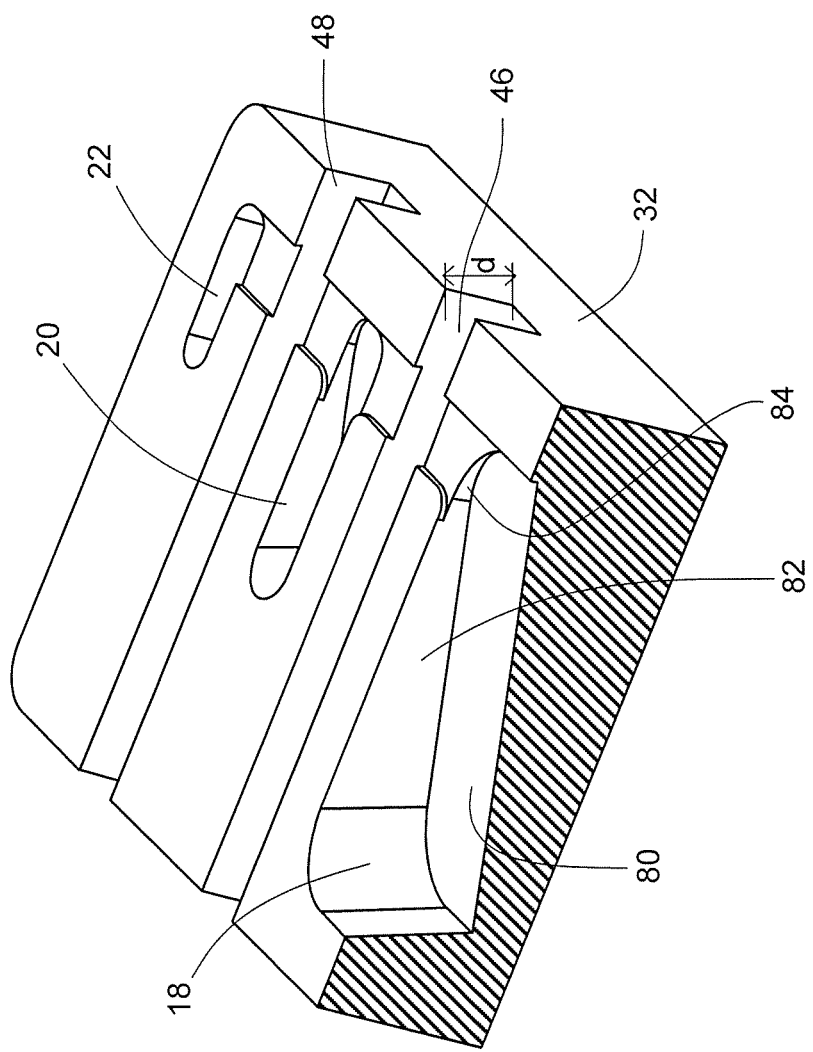
FIG. 2 shows a perspective view of a cross-section taken through one of the chambers in a device.

FIG. 2 shows a perspective view of a cross-section taken through one of the chambers in a device like that shown in FIG. 1. With regard to device 10, the cross-sectional view is taken along the horizontal axis across chamber 18. Adjacent chamber 18 is a channel, and using similar number as in device 10, channel 46. Chamber 20 is positioned between channel 46 and channel 48. Chamber 22 is also visible. The top cover from the device is not included in the view shown in FIG. 2. Each chamber in the device, such as chamber 18, has a floor, such as floor 80 and walls, such as wall 82. In one or all of the chambers the floor has a slope or grade; that is, relative to a fixed horizontal plane through the device, the floor has a change in elevation with horizontally axial distance. Thus, one end of the chamber is deeper, with respect to the top surface of the device, than the opposing end of the chamber; just as a swimming pool has a shallow end and a deep end, chamber 18 in device 10 has a deep end and a shallow end. Each chamber has an opening to its adjacent channel or chamber, as the case may be, and as seen in FIG. 2, chamber 18 has an opening 84 into adjacent channel 46. A skilled artisan can select the slope or percent (%) grade of the floor in each chamber, which can vary from zero (0), i.e., no slope, to 99% where % grade is determined by dividing the elevation difference by the distance between the beginning and end point and multiplying by 100. More preferably, the percent grade is between 1% and 50%, more preferably 1% and 35%. It will be appreciated that one, a portion, or all of the chambers in the device can have a slope. In one embodiment, each chamber in the device expect for the final downstream chamber has a sloped floor.

In one embodiment, wall 82 in chamber 18 is dimensioned to have rounded corners at the deep end of the chamber. That is, the intersection of the walls in the chamber, and in particular the walls at the deeper end of the chamber, have a radius of curvature. Rounded corners assist in control of fluid in the device, particularly as the chamber is filled with a fluid prior to use, to reduce air bubble formation and optimize filling of the chamber from the bottom to the top.

With continued reference to FIG. 2, it is seen in that in the absence of a top cover, channels 46 and 48 are open junctions with a defined depth d, measured from the top surface of the device to the floor of the channel. In one embodiment, the depth of the channel is greater than the depth of the shallow end of its adjacent chamber. Stated in another way, the depth of the channel is greater than the depth of the chamber at the opening between the chamber and the channel. Accordingly, and in one embodiment, at least one chamber in the plurality of chambers in the device has a floor and a side wall, the floor having a slope and the height of the side wall varying with the slope of the floor, to define a chamber with a deep end and a shallow end. Stated alternatively, one or more chambers in the plurality of chambers has a deep end with a depth $d_2$ and a shallow end with a depth $d_1$. A channel disposed between at least two adjacent chambers in the plurality of chambers has a depth greater than $d_1$. This design feature is another means by which movement of fluid in the device is controlled, as during filling of the chamber with a fluid, fluid will flow into the chamber until it encounters the channel (or the opening between the chamber and the channel) and will stop flow in the longitudinal direction in favor of flow out the access port or air vent in the cover (see FIG. 1).

With reference again to FIG. 1, the access ports (e.g., access ports 60, 62, 64, 66, 68 and 70) associated with each chamber in the plurality of chambers 12, 14, 16, 18, 20 and 22, are positioned so fluid is dispensed directly into the deeper end of a chamber. In one embodiment, one or more of the access ports associated with a chamber is positioned for direct introduction of fluid into the deeper portion of the chamber, as opposed to the shallower portion of the chamber adjacent the opening to an adjacent channel. The optional vent associated with each chamber can be positioned at the deeper end of the chamber, in a mid-section of a chamber, or at the shallower end of a chamber.

Figure 3:
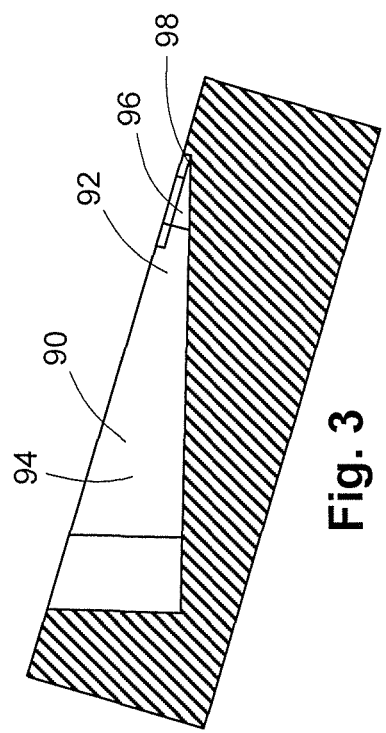
FIG. 3 is a cross-sectional view of a chamber in a device.

FIG. 3 shows a cross-sectional view taken along the horizontal direction through a chamber with a sloped floor in a device. Chamber 90 extends in the horizontal direction along the width of the device from a shallow region 92 to a deeper region 94. An opening 96 provides fluid communication from the chamber to an adjacent structure, typically a chamber or a channel. The deeper region of the chamber has rounded corners, and the shallow region ends in an angled corner 98. The angled corner, which is typically at a 5-30 degree angle, more preferably 7-20 degree angle, is another feature in the device that assists in control of fluid movement during filling of the chamber prior to use and during use. A sharp angle in a corner provides a force the pulls fluid into the corner, achieving a complete or essentially complete fluid fill with minimal air bubble formation.

Figure 4:
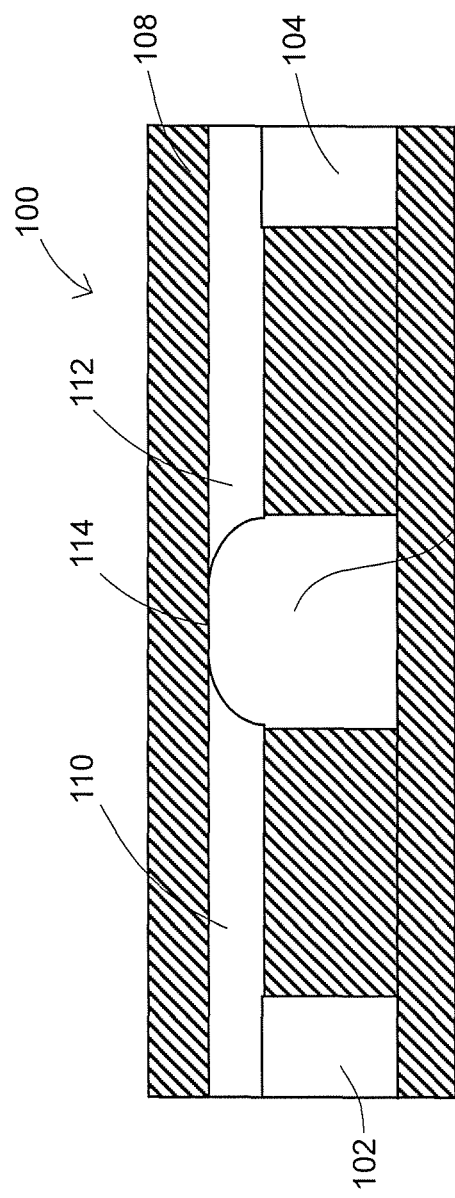
FIG. 4 is a cross-sectional view taken along the longer axis of a device through the gap between adjacent chambers.

FIG. 4 is a cross-sectional view of a device, where the cross-section is taken along the longitudinal axis of a portion of a device, through a channel or "gap" between adjacent chambers. A device 100 comprises a first chamber 102 and a second chamber 104. The first and second chambers are separated by a channel 106. In this view, a top cover 108 is affixed to the device. The top cover when placed on the device defines channel 106, dimensionally changing it from an open trench to a closed channel. The top cover when in place on the device, also defines a capillary opening or conduit 110 for fluid communication between chamber 102 and channel 106. As seen in FIG. 4, chamber 102 and conduit 110 are filled with a fluid. When the fluid reaches channel 106, which is filled with a gas (e.g., air, nitrogen, other inert gas), fluid flow halts. Similarly, chamber 104 and conduit 112 are filled with a fluid (liquid), and typically a different fluid than the fluid in chamber 102 and conduit 110. When the fluid in chamber 104 fills conduit 112 and reaches channel 106 which is filled with a gas (e.g., air), fluid (liquid) flow halts. The air in channel 106 prevents mixing of the two different liquid fluids in chambers 102 and 104, and their respective conduits 110, 112. This is another design feature of the device that provides liquid fluid control, in this case by preventing undesired mixing of fluids in adjacent chambers.

During placement of liquid into a chamber, liquid flows from the chambers into the conduits (110 or 112, depending on the chamber being filled). Flow of fluid is stopped by the sharp edges on the sides and bottom of the chamber (as discussed above) as it travels toward the air-filled channel 106. As can be seen in FIG. 4, the cover extends across the conduits 110, 112, and a slit 114 is defined at the intersection of channel 106 and the cover. Surface tension causes fluid in a chamber to extend beyond the conduits 110, 112 and travel along the underside of the cover, and potentially into slit 114. The distance the fluid extends into the slit is a function of the surface energy properties of the liquid and of the material from which the cover is made. If the slit is too narrow, the fluids in adjacent chambers may undesirably contact one another and mix if the fluids are not immiscible. During use of the device (described below), fluid from one chamber can be displaced across the slit resulting in cross-talking of fluid between chambers.

In a preferred embodiment, channel 106 and slit 114 defined by the cover and the channel is filled with air. In other embodiments, channel and slit are filled with a water-immiscible substance, such as a lipophilic material, like an oil. Exemplary water-immiscible materials are set forth in U.S. Pat. Nos. 8,187,808 and 8,206,918, which are incorporated by reference herein in their entireties. The "water-immiscible fluid" is a liquid or semisolid fluid that phase separates when diluted with an equal part of water; preferably, the fluid phase separates when diluted 2:1, 4:1, or 10:1 with water. More preferably, the water-immiscible fluid is substantially fully immiscible with water; it is preferably immiscible with lower alcohols as well. Examples of suitable water-immiscible fluids include lipophilic fluids such as waxes, preferably liquid waxes such as Chill-Out™ 14 wax (MJ Research), and oils, such as mineral oil, paraffin oil, or silicone, fluorosilicone, or fluorocarbon oils. Semisolid waxes may also be used, as long as the external force applied is sufficient to move the solid phase carrier through the medium; heat may be applied to reduce viscosity. In general, however, waxes and oils that are liquid at room temperature are preferred. Also suitable are, for example, hydrocarbon solvents such as toluene, hexane, or octane, and polar hydrophobic solvents such as 1,4-dioxane, acetonitrile, tert-butanol or higher (up to about C12) alcohols or acetates, cyclohexanone, or t-butyl methyl ether. (If a polar hydrophilic solvent is employed, the water-miscible liquid reagents employed in the device preferably do not include substantial amounts of lower alcohols.) Preferably, the water-immiscible fluid has a low vapor pressure and a specific gravity less than that of water. In selected embodiments, the water-immiscible fluid is an oil, such as mineral oil.

Figure 5:
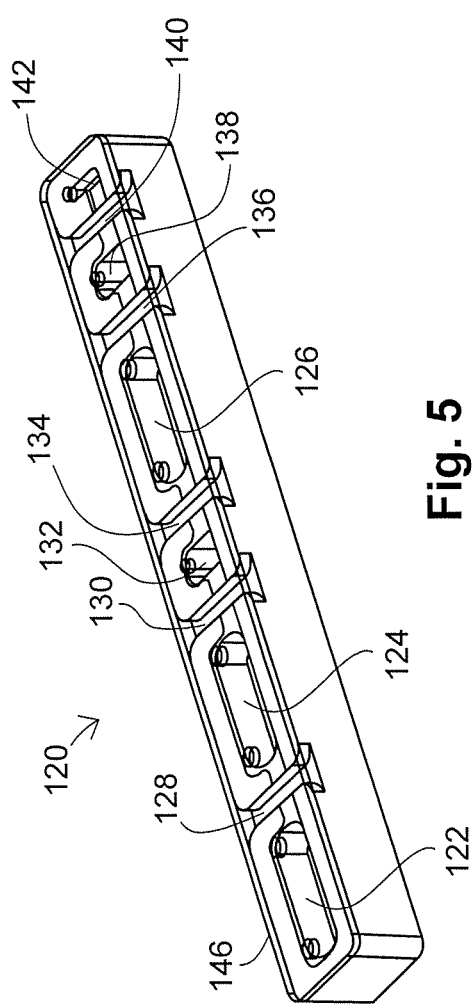
FIG. 5 is a device in accord with another embodiment.

FIG. 5 illustrates a device 120 in accord with another embodiment, the device finding use in manual, semi-automatic or automated extraction/isolation of a target analyte from a sample. Device 120 comprises a plurality of chamber in series. In this embodiment, the device is fabricated to define chambers 122, 124, and 126, each chamber dimensioned to contain a selected volume of a fluid. The chambers need not be of the same dimensions geometrically or volumetrically, but can be tailored to suit a particular extraction procedure. In an exemplary embodiment, for isolation of a protein or a nucleic acid from a biological sample, chamber 122 contains a reagent for lysis of cells in the sample, chamber 124 contains a wash solution (a buffer or salt solution), and chamber 126 contains a second wash solution (a buffer or salt solution). Disposed between chamber 122 and chamber 124 is an air-filled conduit 128. Positioned after chamber 124 and before chamber 126 is a first air-filled conduit 130, a reservoir containing a water-immiscible substance 132, and a second air-filled conduit 134. Serially positioned downstream (to the right in FIG. 5) of chamber 126 is an (third) air-filled conduit 136, a (second) reservoir containing a water-immiscible substance 138, and an (fourth) air-filled conduit 140. An elution chamber 142 is downstream of air-filled conduit 140, the elution chamber also containing a liquid reagent.

The chambers, conduits and reservoirs positioned serially along a longitudinal axis of the device are in fluid communication via openings between each adjacent structure (chamber, conduit or reservoir). The communication permits travel of a solid carrier from one chamber to the next, as will further be described below. The air-filled conduits, or air-gaps, between chambers and reservoirs are positioned to control fluid flow, to inhibit undesirable mixing of the different fluids in the chambers and reservoirs, so that each chamber serves its function with high accuracy and precision in isolation of the target analyte from the sample.

The device in FIG. 5 also comprises a cover 146, with a plurality of openings in the cover, to permit introduction of fluids into the chambers and reservoirs, as discussed above.

Figure 6:
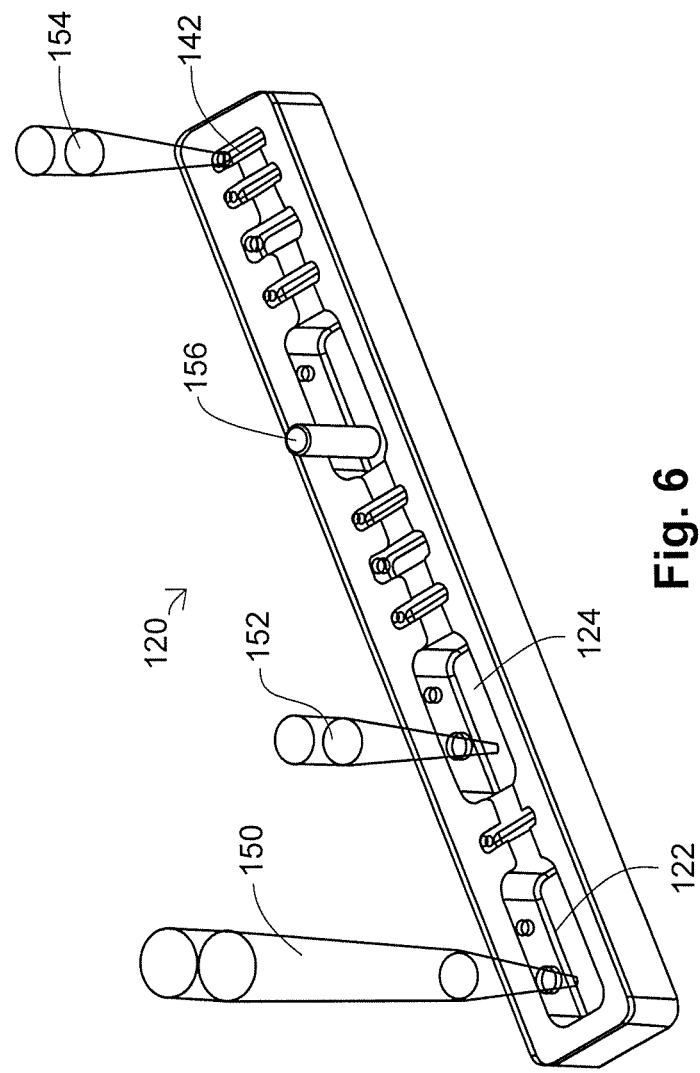
FIG. 6 shows a device in accord with another embodiment, where dispensing pipettes are shown interacting with some chambers in the device.

FIG. 6 shows a device like that described in FIG. 5, during use in a manual operation. Device 120 is shown with a pipette tip 150 inserted into an opening in the cover, the opening providing access to chamber 122. A pipette tip 152 is inserted into an opening in the cover that provides access to chamber 124, and a pipette tip 154 is inserted in an opening in the cover to provide access to chamber 142. The pipette tips when operably connected to a pipette permit introduction of a liquid reagent into a respective chamber. A similar approach of insertion of an implement, like a pipette tip or a syringe, into an opening associated with each chamber and reservoir permits placement of reagent fluid in the device. The fluids can be introduced into the device in any order, and in preferred embodiments, wash fluids are introduced before a lysis fluid, and the fluid in the final downstream chamber, typically an elution or detection chamber, is introduced before the water-immiscible substance is introduced into their respective reservoirs.

Contained within a first chamber of the device, or introduced by a user, is a plurality of solid carriers. The solid carrier is capable of association with the target analyte, by virtue of an ionic interaction or a binding interaction. In one embodiment, the solid carrier is a magnetic bead; in other embodiments, the solid carrier is a polymeric bead with a surface coating of a binding member or a substance that interacts with the target analyte. A sample introduced into the chamber of the device containing the particles initiates an interaction between the solid carrier and the analyte of interest in the sample. By way of example, solid carriers in a chamber of the device comprising a lysis reagent initiates release of nucleic acid or protein from a cell, both being capable of interaction with the solid carriers. Using an applied external force, such as a magnet externally positioned from the device, exemplified by magnet 156 in FIG. 6, the solid carrier (in this embodiment, magnetic beads) are transferred from one chamber to the next, e.g., from a first to a second chamber, such as from chamber 122 to chamber 124. Movement of the external magnet effects movement of the magnetic particles in a chamber, and transfer from one chamber to an adjacent chamber transverses any intervening air-filled conduits and/or water-immiscible filled reservoirs. As the solid carriers transverse these structures, fluid trapped on the external surfaces of the solid carrier is deposited in the air-filled conduits and/or water-immiscible filled reservoirs, preventing cross-talk or cross-contamination of fluids in adjacent reservoirs. This permits the chambers to be designed to hold microliter amounts of fluid, reducing the overall size of the device and, importantly, the size of sample needed for processing. In one embodiment, the chambers are dimensioned to contain between 200-1000 microliters, preferably between 300-800 microliters, more preferably between 500-750 microliters. The elution/detection chamber is dimensioned to contain between 15-75 microliters, more preferably between 20-40 microliters. Also, as the solid carriers transverse these structures, the fluids in the chambers preferably remains stationary.

As mentioned above, in the extraction/isolation procedures described herein, a solid carrier member is used to associate with the analyte of interest. In some embodiments, a specific binding member is attached to a solid phase support to accomplish the interaction. In other embodiments, the solid carrier is manufactured from a material that has an ionic interaction with the analyte of interest. A "specific binding member" or "affinity reagent", as used herein, is a molecule or moiety that specifically binds to a target analyte through chemical or physical means. Immunoreactive specific binding members include antigens or antigen fragments and antibodies or functional antibody fragments. Other specific binding pairs include biotin and avidin, carbohydrates and lectins, complementary nucleotide sequences, effector and receptor molecules, cofactors and enzymes, enzyme inhibitors and enzymes, and the like. In one embodiment, the solid carrier is a plurality of paramagnetic particles, in order to extract the analyte from a sample containing non-target components. Following isolation of the particle-analyte complex from the non-target components, the complex is treated to effect removal of the analyte from the particles. Removal may be effected by, for example, heating the solution containing the complex and/or changing the chemical environment (e.g. salt concentration, pH, etc.). In other embodiments, a chemical or enzymatic reagent is used to disrupt the particle-analyte complex and thus effect removal of the analyte from the particles.

Particular examples of systems designed for formation of specific particle-analyte complexes and their subsequent release of analyte include, for example, the MagneHis™ protein purification system (Promega Corp., Madison, Wis.), in which paramagnetic precharged nickel particles (MagneHis™ Ni-Particles) are used to isolate polyhistidine- or HQ-tagged proteins from a sample matrix such as a cell lysate. Also preferred are functionalized solid supports as described in U.S. Pat. No. 7,354,750 (D. J. Simpson et al., Promega Corp.). Alternatively, the MagneGST™ protein purification system (Promega Corp.) employs immobilized glutathione paramagnetic particles (MagneGST™ Particles) to isolate glutathione-S-transferase (GST) fusion proteins. In the HaloTag® protein purification system (Promega Corp.), useful for purification of recombinant proteins, the protein of interest is expressed as a fusion protein, fused to a HaloTag® protein tag, which covalently binds to a HaloLink™ solid support via an immobilized chloroalkane ligand. Following separation of the fusion protein-resin complex from other matrix components, a specific protease then cleaves the target protein from the fused tag and the resin. The protease is also tagged such that it will remain bound to the resin.

In one embodiment, the device herein comprises a plurality of magnetic particles (not shown in the Figures). The device may be supplied with the particles, or they may be added to the first chamber prior to or during use. The solid carrier particles are able to pass through the chambers and flow paths upon application of an external force. In one embodiment, the particles are magnetic or paramagnetic particles, and the external force is a magnetic force.

At least a plurality and preferably all of the particles comprise a surface affinity reagent, as defined above, which is effective to specifically and reversibly bind the target analyte; e.g. by specific antibody-antigen binding, by hybridization, by ionic or hydrogen bonding, or by other chemical interaction. The binding moiety may be, for example, a nucleic acid probe sequence, effective to hybridize to a target nucleic acid sequence, or an antibody or functional fragment thereof, effective to bind a target protein or other analyte. Any binding moiety of any desired specificity may be used.

With continuing reference to FIG. 6, the externally applied force is moved manually (although it can be automatic, if desired) from one chamber to the next, transferring the solid carriers from one chamber to the next, for treatment by the fluid reagent in each chamber. During the transferring, fluid in the chambers remains stationary. In the elution/detection chamber, the analyte of interest is isolated from the sample, and the carrier and analyte of interest are the predominate species present. In one embodiment, the analyte of interest can be detected in situ in the detection chamber. In embodiments where the analyte is a nucleic acid, the elution chamber can contain necessary reagents for polymerase chain reaction of the isolated nucleic acid, to amplify the nucleic acid for detection in situ. In another embodiment, the analyte of interest is removed from the elution/detection chamber for subsequent processing—for example, amplification by polymerase chain reaction.

In one embodiment, the analyte of interest is eluted off of the solid carrier member(s), which is/are regenerated for reuse, and moved by pipette or magnetic force into the first chamber for a subsequent extraction/isolation process. Other variations of using the device are set forth in U.S. Publication Nos. 2011/0213133, 2013/0158240 and 2011/0212509, which each are incorporated by reference herein.

Figure 7:
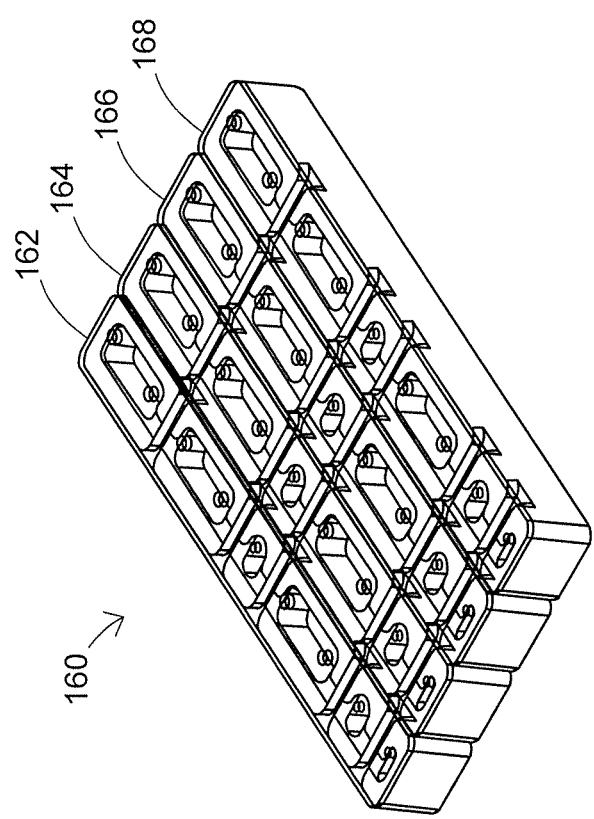
FIG. 7 shows a device in accord with another embodiment, for use in high throughput and multiplexing applications.

FIG. 7 shows an embodiment of a device intended for high throughput and multiplexing applications. Here, device 160 is comprised of four processing units 162, 164, 166, and 168. Each of the processing units comprises a series of chambers, conduits and reservoirs, like that described with respect to any one of FIGS. 1, 5 and 6 herein. Device 160 permits processing of a plurality of samples, and in the embodiment the plurality is four samples, in parallel. It will be appreciated that any number of processing units can be combined into the device to process in parallel a plurality of samples, where the plurality is any desired number (e.g., 4, 6, 8, 10, 12, 16, 24, etc).

The chambers in the devices described herein contain reagents for processing the sample to isolate the species of interest. The reagents can be placed in the chambers in dried form or in lyophilized form, and a liquid medium added via the access ports in the cover to hydrate and solubilize the reagents. The reagents can be introduced into the chambers as a fluid prepared off-line and external from the device. Reagents can also be introduced into the chambers and reservoirs by external packaging units, such as those described in U.S. Patent Application Publication No. 2012-0107811, which is incorporated by reference herein in its entirety. The external packaging units are preferably burstable packaging units attachable to the device for introduction of a reagent stored in the packaging unit into a chamber via an opening in the cover or bottom of the device.

In one embodiment, a high-throughput device, like that shown in FIG. 7, is for use in high-throughput DNA (or RNA) sequencing (also termed next-generation sequencing), where DNA is isolated from the sample, amplified, and detected. In one embodiment, reversible dye-terminators are used, extending the DNA one nucleotide at a time. A camera positioned for viewing the detection chamber takes images of fluorescently-labeled nucleotides, then the dye along with a terminal 3' blocker is chemically removed from the DNA, allowing the next cycle. In one embodiment, the device described herein is a part of a system comprised of the device and a liquid handling apparatus, where the device is configured to be inserted on a platform of the liquid handling apparatus and the openings in the cover of the device are positioned for interaction with the liquid dispensing implements on the liquid handling apparatus.

Accordingly, the devices described herein are contemplated for use in a method for extracting (or isolating) an analyte of interest from a sample. The method comprises providing a device as described herein and introducing a sample into a first chamber of the device. The first chamber of the device or the sample upon its introduction into the device comprises a solid carrier member, or a plurality of solid carriers, capable interacting with an analyte of interest in the sample, thus forming a carrier-analyte complex in the first chamber. The carrier-analyte complex(es) is/are moved from the first chamber into a second, downstream chamber by an externally applied force that interacts with the solid carrier. Movement from the first chamber to downstream chambers causes the carrier-analyte complexes to transverse one or more channels in the device. In some embodiments, the channel between two chambers is filled with a gas, such as air, and in other embodiments, the channel between two chambers is filled with a water-immiscible liquid. In some embodiments, a chamber in the device comprises a water-immiscible liquid. Movement of the carrier-analyte complexes across a gas-filled chamber and/or into and through the water-immiscible liquid separates the complexes from the sample, isolating the undesired fraction of the sample from the fraction bound to the solid carrier members.

Figure 8:
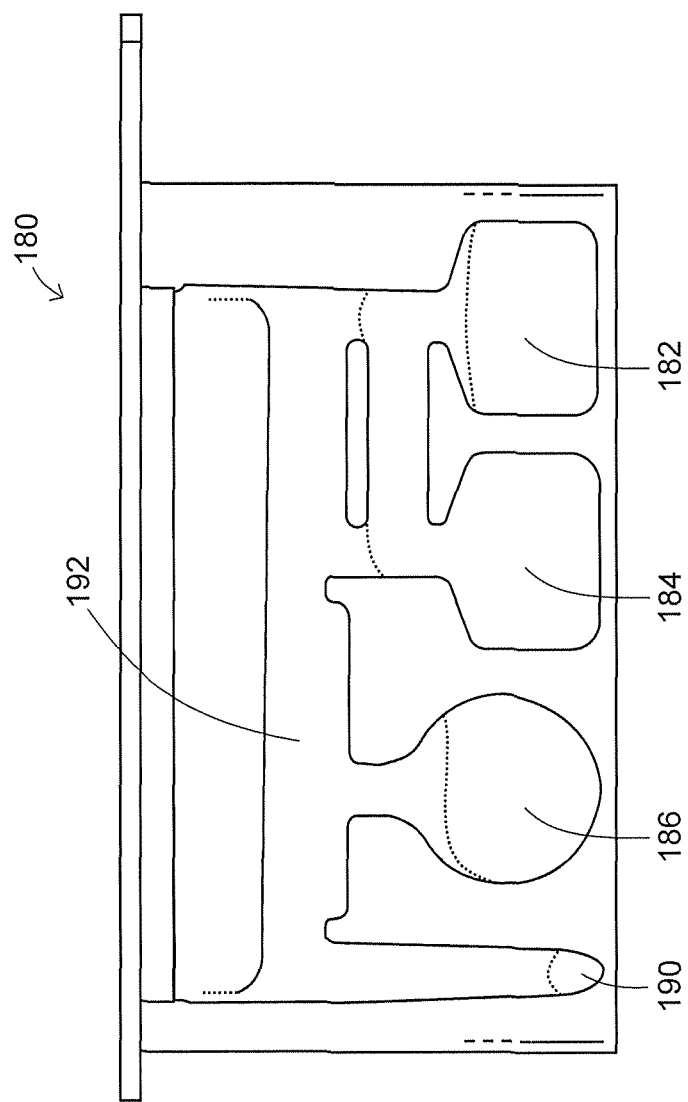
FIG. 8 shows a device in accord with another embodiment.

FIG. 8 shows a device in accord with another embodiment, where a cartridge 180 is comprised of a first chamber 182, a second chamber 184, and a third chamber 186. A fourth chamber 190 is for elution of an isolated species, and optional detection in situ. The chambers in the device are in fluid communication by a channel 192. A subchannel 194 fluidly connects chambers 182 and 184. In use, and as shown in FIG. 8, each chamber is filled with a fluid and the channel and sub-channels are also filled with a fluid. The channel 192 is filled with a water-immsicible substance, and the subchannel 194 is filled with a wash reagent that fills chamber 184 and that overlays a lysis reagent in chamber 182. The water-immiscible substance overlays the wash reagent in chamber 186, and an elution medium in chamber 190. Solid carrier particles in the lysis chamber are moved into the wash chamber either by way of the subchannel or the water immiscible substance-filled channel. From the wash chamber 184, the solid carrier particles with associated analyte of interest are transferred through the stationary water immiscible substance into the wash chamber 186. Next, the solid carrier particles with associated analyte of interest are moved through the stationary water immiscible substance into the elution chamber. The fluids in the chamber and the channels remain essentially stationary during the extraction process.

Figure 9:
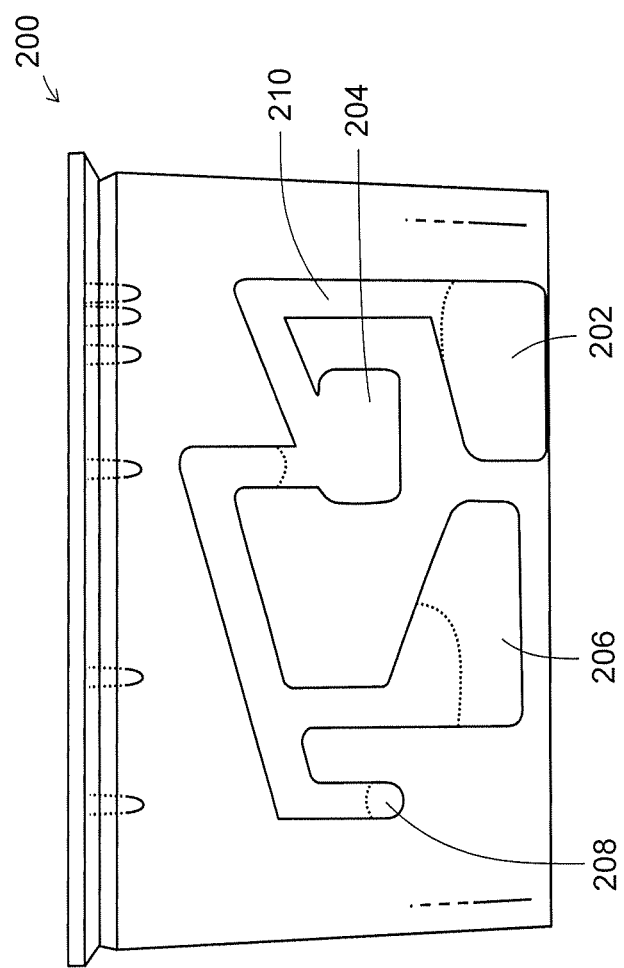
FIG. 9 shows yet another device in accord with other embodiments.

FIG. 9 shows yet another device in accord with other embodiments. Device 200 comprises a plurality of chambers, identified as chambers 202, 204, 206 and 208. The chambers are fluid communication via a fluid flow path 210 that travels from a first chamber 202 into a second chamber 204. The fluid flow path between these chambers, in one embodiment, contains a wash buffer that is also present in the second chamber. The fluid flow path continues between the second chamber to the third chamber 206 and then into the fourth chamber 208. The fluid flow path between the second, third and fourth chambers contains a stationary water-immiscible substance. During movement of solid carrier particles along the flow path, the fluids in the chambers and/or flow path are stationary.

Figure 10A:
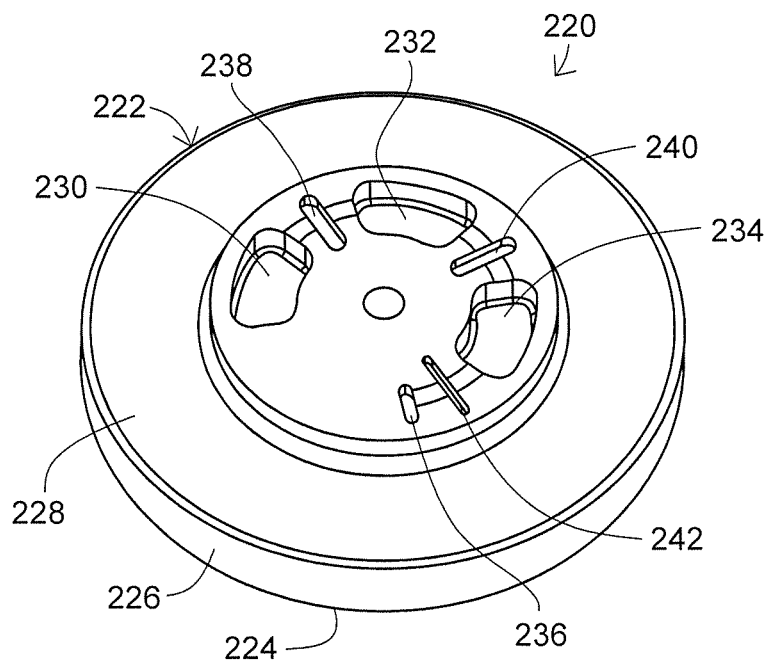
FIGS. 10A-10C illustrate another device according to still other embodiments.
Figure 10B:
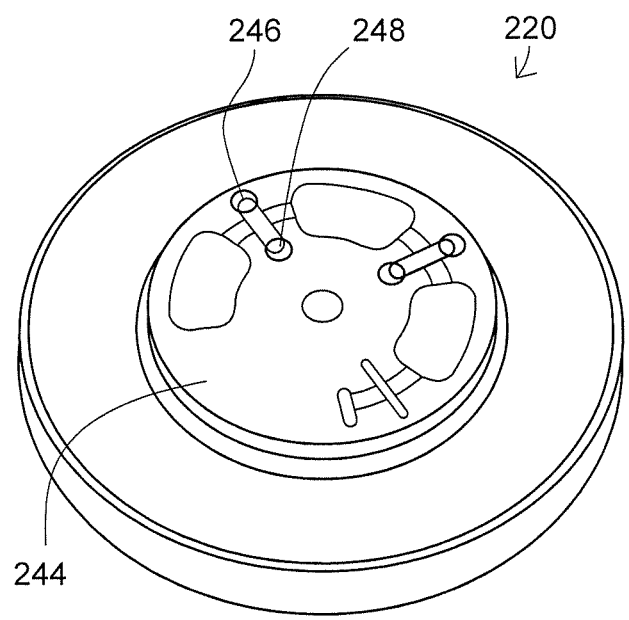
Figure 10C:
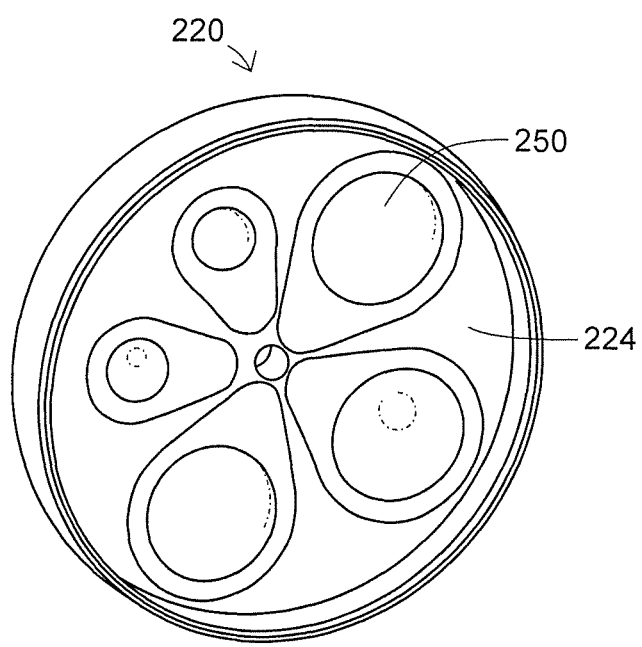

It will be appreciated that although the embodiments of the devices described herein above are linear, the planar device in other embodiments is circular. An embodiment of such a device is illustrated in FIGS. 10A-10C. Device 220 comprises a housing member 222 with a bottom 224, a side wall 226 and a top 228. Formed within the housing member is at least two chambers, shown in this embodiment are a first chamber 230, a second chamber 232, a third chamber 234 and a fourth chamber 236. The chambers are in fluid communication, so that a sample and solid carrier dispensed into one of the chambers, for example, the first chamber, can be moved serially from one chamber to the next. The chambers are separated by air-filled gaps or by reservoirs filled with a water-immiscible substance. In the embodiment shown in FIG. 10A, chamber 230 and chamber 232 are separated by a slot or gap 238 that is filled with a gas, preferably air. It will be appreciated that the slot or gap may also be filled with a fluid. Slot 240 is positioned between chambers 232 and 234, so that transfer of a plurality of solid carriers associated with an analyte of interest (a carrier-analyte complex) passes through slot 240 as it moves from chamber 232 to chamber 234. Positioned between chamber 234 and chamber 236 is a reservoir 242 that is preferably filled with or containing a water-immiscible substance.

Movement of a carrier-analyte complex from a first chamber to subsequent chambers, passing through the air-filled gaps and/or water-immiscible substance, is achieved by application of an externally applied force and relative movement of the device with respect to the force, or vice versa. That is, the force can be moved while the device remains stationary, or the device can be rotated or moved while the force remains stationary. The same is applicable, of course, for any of the linear configurations of the device described above.

FIG. 10B shows device 220 with a rotatable and movable top plate 244 positioned on the top of the device. The top plate 224 comprises one or more ports, such as ports 246, 248. The top plate can be rotated so that one or both of ports 246, 248 provide access to a particular chamber. Through the ports, fluids for processing a sample and for extracting the analyte of interest can be introduced.

FIG. 10C shows a bottom view of device 220, where in this embodiment the device includes a plurality of reagent packaging units affixed to the bottom of the device, such as unit 250. The packaging units are filled with a liquid reagent and are aligned over an access port in the bottom of the device, so that fluid in the packaging unit can be transferred via the access port into a chamber or reservoir of the device.

It will be appreciated that the circular device of FIGS. 10A-10C can include any or all of the features described above with respect to the linear embodiment of the device for fluid control. For example, one or more of the chambers can have a slope in the floor of the chamber, giving the device a three-dimensional fluid movement. After filling the chambers and reservoirs in the device of FIGS. 10A-10C with a desired reagent, the reagent remains essentially stationary as the carrier-analyte complex is transported from one chamber to the next.

During use of any of the devices described herein, a protocol for movement of the plurality of solid carriers from one chamber to the next is contemplated. The movement protocol is achieved by defined movement of the externally applied force or forces that effects movement of the solid carriers. Certain movements loosen the pellet of solid carriers that forms in the presence of the applied force, maximizing exchange of fluid surrounding and encapsulated by the pellet of solid carriers.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A device, comprising
   a first plurality of chambers disposed along a longitudinal axis of the device, one or more chambers in the first plurality of chambers having both a deep end and a shallow end arranged orthogonally to the longitudinal axis, the shallow end with a depth $d_1$, wherein the deep end is adjacent to a side of the chambers; and
   a channel disposed between and in fluid communication with at least two adjacent chambers in the first plurality of chambers, the channel having a depth greater than $d_1$.

2. The device of claim 1, wherein the chambers in the first plurality of chambers are serially positioned and separated by a channel.

3. The device of claim 2, wherein the first plurality of chambers is comprised of at least three chambers, wherein two chambers in the first plurality have a deep end and a shallow end arranged orthogonally to the longitudinal axis, the shallow end with a depth $d_1$, and wherein the channel is disposed between the two chambers having the shallow end with a depth $d_1$.

4. The device of claim 2, wherein the first plurality of chambers is comprised of at least five chambers, wherein three chambers in the first plurality have a deep end and a shallow end arranged orthogonally to the longitudinal axis, the shallow end with a depth $d_1$, and wherein the channel is disposed between two chambers having the shallow end with a depth $d_1$.

5. The device of claim 1, wherein each chamber in the first plurality of chambers has a volume, and wherein the volume of one chamber in the plurality of chambers differs from the volume of another chamber in the first plurality.

6. The device of claim 1, wherein the one or more chambers in the first plurality of chambers has a floor and a side wall that meet to define four corners, wherein at least the corners in the deep end of the chamber are rounded.

7. The device of claim 1, wherein the one or more chambers in the first plurality of chambers has a floor and a side wall that meet to define four corners, wherein at least the corners in the shallow end of the chamber are angled.

8. The device of claim 1, further comprising a cover, the cover having an access port in fluid communication with a chamber in the first plurality of chambers.

9. The device of claim 8, wherein the access port is in fluid communication with the one or more chambers in the first plurality of chambers and wherein the access port is positioned for introduction of fluid directly into the deep end of the chamber.

10. The device of claim 1, further comprising:
    a second plurality of chambers, one or more chambers in the second plurality of chambers having a deep end and a shallow end arranged orthogonally to the longitudinal axis, the shallow end with a depth $d_1$; and
    a channel disposed between at least two adjacent chambers in the second plurality of chambers, the channel having a depth greater than $d_1$.

11. The device of claim 10, wherein the first and second plurality of chambers are linearly parallel.

* * * * *